United States Patent [19]

McCartney

[11] Patent Number: 4,711,522

[45] Date of Patent: Dec. 8, 1987

[54] OPTICAL CATHETER

[75] Inventor: Ronald L. McCartney, Orange, Calif.

[73] Assignee: American Hospital Supply Corporation, Deerfield, Ill.

[21] Appl. No.: 781,411

[22] Filed: Sep. 27, 1985

Related U.S. Application Data

[63] Continuation-in-part of Ser. No. 546,500, Oct. 28, 1983, abandoned.

[51] Int. Cl.[4] .............................................. G02B 6/38
[52] U.S. Cl. .................................... 350/96.21; 350/96.20
[58] Field of Search ................ 350/96.20, 96.21, 96.22

[56] References Cited

U.S. PATENT DOCUMENTS

| 4,026,633 | 5/1977 | Crick | 350/96.21 |
| 4,140,367 | 2/1979 | Makuch et al. | 350/96.22 |
| 4,186,997 | 2/1980 | Schumacher | 350/96.21 |
| 4,201,222 | 5/1980 | Haase | 128/634 |
| 4,477,146 | 10/1984 | Bowen et al. | 350/96.2 X |
| 4,515,434 | 5/1985 | Margolin et al. | 350/96.2 X |
| 4,538,609 | 9/1985 | Takenaka et al. | 350/96.20 X |
| 4,582,392 | 4/1986 | Williams et al. | 350/96.2 |

OTHER PUBLICATIONS

"A New Fibre-Optic Liquid Crystal Catheter for Oxygen Saturation and Blood Flow Measurements in the Coronary Sinus", D. De Rossi et al., *Journal of Biomedical Engineering*, 1980, vol. 2, Oct., pp. 257-264.

*Primary Examiner*—John Lee
*Assistant Examiner*—Michael Menz
*Attorney, Agent, or Firm*—Gordon L. Peterson

[57] ABSTRACT

An apparatus comprising a connector body, an optical fiber mounted on the connector body and a receptacle having a cavity for receiving the connector body. The connector body has a cam surface, and the receptacle cooperates with the cam surface when the receptacle and connector body are appropriately positioned to urge the connector body upwardly and farther into the cavity to place optical portions of the connector body and the receptacle into substantial engagement.

24 Claims, 24 Drawing Figures

OPTICAL CATHETER

This application is a continuation-in-part of application Ser. No. 546,500 filed Oct. 28, 1983, (abandoned) and entitled OPTICAL CATHETER.

BACKGROUND OF THE INVENTION

Fiber optics are used in catheters and probes for the purpose of transmitting light into and receiving light from internal regions of the body. Because a catheter or probe must be sized to be received within a vein or artery, the fiber optics used within such an apparatus must also be of very small diameter.

For example, a catheter or probe may include an elongated tube having proximal and distal openings and fiber optic means in the form of one or more fiber optic light conductors in the passage and extending through the proximal opening to provide a proximal section of the fiber optic means outside of the tube. The fiber optic means is coupled to a connector body, and the connector body is received within a cavity of a receptacle which optically couples the catheter to an instrument. The receptacle may be considered as part of the instrument. The instrument may, for example, provide a source of light for transmission through the catheter and the necessary equipment to process a light signal received from the catheter.

One problem with this construction is the mounting of the fine fiber optic light conductors on the connector body. The fiber optic light conductors each of which comprises one or more optical fibers, must be located with respect to the connector body with great precision and securely retained in position. This is necessary so that light can be transmitted efficiently between the instrument and the catheter. Locating the fiber optic light conductor on the connector body with precision is difficult because of the small diameter of the optical fibers.

It is also important to assure that the connector body is tightly seated within the receptacle. If this is not done, losses will occur at the interface. Moreover, the connector body and receptacle must cooperate with each other to precisely position the connector body within the receptacle to maximize the optical coupling between the optical fibers in the connector body and in the receptacle.

More specifically, it is important that the connection of the connector body to the receptacle be stable so as to preclude, insofar as possible, relative movement between the connector body and the receptacle of the type which would effect the optical signal. It is also important that the coupling of the connector body to the receptacle provide reproduceability, i.e., provide the same relative orientation of these two members each time the connector body is inserted into the receptacle so that the optical signal provided does not vary as a result of reinsertion of the connector body into the receptacle.

In one prior art device, the connector body is held within the receptacle by a spring door. This prior art device does not provide the stability and reproduceability that are desired. In addition, the spring door can be difficult to clean, thereby making reuse of the receptacle somewhat more difficult.

SUMMARY OF THE INVENTION

With this invention, the optical portions of the connector body are accurately guided into confronting relationship with the optical portions of the receptacle. This is accomplished in a way to provide the resulting connection with stability and reproduceability. The connector body snaps into the receptacle with an audible "click" so that the operator is made aware that the connector body is fully and correctly seated in the receptacle so that false locking is not likely to occur. In addition, the connector may have multiple operative positions within the receptacle, and the receptacle can be easily cleaned.

With the invention of parent application Ser. No. 546,500, (abandoned) the connector body and the receptacle cooperate to pull the connector body into the receptacle to optically couple the optical portions of the connector body and the receptacle. This invention retains this important feature. In addition, with the present invention, the connector body is urged, not only forwardly, but also in another direction so that the connector body can be positively driven against multiple stops or surfaces lying in different planes on the receptacle so that the connector body is stably held in position and a reproducible connection is obtained.

This invention is applicable, for example, to an apparatus comprising a connector body having an exterior or forward face and a fiber optic light conductor mounted on the connector body with an end of the fiber optic light conductor being adjacent the face and capable of transmitting light to or from a location on the face. A receptacle is used to optically couple the fiber optic light conductor to an instrument. The receptacle has a cavity with an open end for receiving the connector body, a face partly defining the cavity and means for transmitting light to or from a location on the face of a receptacle.

The connector body is inserted into the cavity of the receptacle in a generally forwardly direction. With this invention, the receptacle cooperates with the connector body to urge the connector body farther into the cavity to place the above-mentioned locations on the faces in substantial engagement. This can be advantageously accomplished by providing a cam surface on the connector body and biasing means on the receptacle for cooperating with the cam surface to provide the driving force. With this construction, the biasing means acts on the cam surface when the above-mentioned locations are nearly in engagement to drive the connector body completely into the cavity to place such locations in substantial engagement. The cam surface and the biasing means may also retain the connector body in the cavity of the receptacle.

In a preferred construction, the connector body has a recess or groove on its exterior surface, and the groove is partly defined by the cam surface. In this event, the biasing means may include a projection on the receptacle which is receivable in the groove. Of course, the groove and projection may be on the receptacle and connector body, respectively, if desired. In a preferred construction, the biasing means includes spaced regions of the receptacle on opposite sides of the cavity, and thre receptacle is sufficiently resilient to allow the spaced regions to be resiliently spread farther apart so that they can apply an inwardly directed biasing force.

The cam surface cooperates with the projection for urging the connector body in a direction or along a path which has components which extend farther into the cavity and in another direction. This other direction may be defined in various ways. For example, this other direction is generally transverse to both the forwardly direction and the biasing direction, i.e., the direction in which the projection is resiliently urged by the receptacle. Alternatively, these components may be considered as extending toward the forward face of the connector body and in a first direction where the first direction is the direction in which top and bottom surfaces of the connector body ar spaced.

The urging of the connector body in the desired direction can be accomplished, for example, by providing the cam surface with an inclined surface being engageable with the projection. Preferably, the cam surface is on a side wall of the connector body, and the recess is at least partially closed at the end adjacent the inclined surface. To facilitate molding, the other end of the recess preferably opens at an edge of the side wall.

The projection can advantageously include a pin which is harder than the material of the connector body engaged by the pin so that the pin can, to some degree, form its own seat on the softer material of the connector body. Preferably, the pin has a somewhat flat head to minimize deformation of the connector body outside of the recess as a result of sliding the connector body into the cavity of the receptacle.

To help provide stability and reproduceability, the connector body is urged against the face of the receptacle and a stop on the receptacle. The stop and the face are generally transverse to each other and so the connector body is stably retained by virtue of the cooperation between the projection and the recess which urge the connector body against these two transverse surfaces.

This invention is particularly adapted for optically coupling multiple optical fibers carried by the connector body with multiple optical fibers carried by the receptacle. When so used, the ends of the optical fibers carried by the connector body are preferably spaced apart in the same general direction as the side surfaces or side walls of the connector body. When so arranged, the urging of the connector body against the two transverse surfaces as described herein will not tend to significantly cock any of the optical fiber ends on the connector body away from the associated optical fibers carried by the receptacle.

To properly align the optical protions of the connector body and the receptacle, guide means at least partially on the receptacle guide the connector body along a path in the cavity. The guide means advantageously defines the path so that it has a first section extending in a first direction and a second section extending in a second direction, with the second section of the path being closely adjacent the face of the receptacle. In a preferred construction, the guide means includes a cam surface on the face of the receptacle and a cam follower surface on the face of the connector body. The surfaces on such faces define the second section of the path. The above-described cooperation of the biasing means and the cam surface urges the connector body along at least a portion of the second section of the path.

The multi-direction path is useful in accurately orienting the optical portions of the connector body and the receptacle. The cam follower surface is accurately positioned in relation to the end of the fiber optic light conductor without any accumulation of tolerances, and this helps assure accurate orientation of the optical portions of the connector body in relation to the receptacle.

The invention is particularly adapted for use in a catheter or probe which includes an elongated tube sized to be received within a vein or an artery and having a passage with proximal and distal openings. In this event, fiber optic means is partially in the passage and extends through the proximal opening to provide a proximal section outside of the tube which is coupled to the connector body.

The fiber optic means may include one or more fiber optic light conductors, each of which may include one or more optical fibers. One of the exit passages in the connector body is provided for each of the fiber optic light conductors.

The invention, together with additional features and advantages thereof, may best be understood by reference to the following description taken in connnection with the accompanying illustrative drawing.

BRIEF DESCRIPTION OF THE DRAWINGS

FIGS. 9 and 9a are fragmentary, sectional views similar to FIGS. 2 and 2a, respectively, of another embodiment of the invention, with the connector body in the self-test and monitor positions, respectively.

FIG. 10 is a fragmentary, sectional view taken generally along line 10—10 of FIG. 9a.

FIG. 12 is a fragmentary, sectional view taken generally along line 12—12 of FIG. 11.

FIG. 14 is an end elevational view taken from the left end of FIG. 10.

DESCRIPTION OF THE PREFERRED EMBODIMENT

Figures 1, 1A:
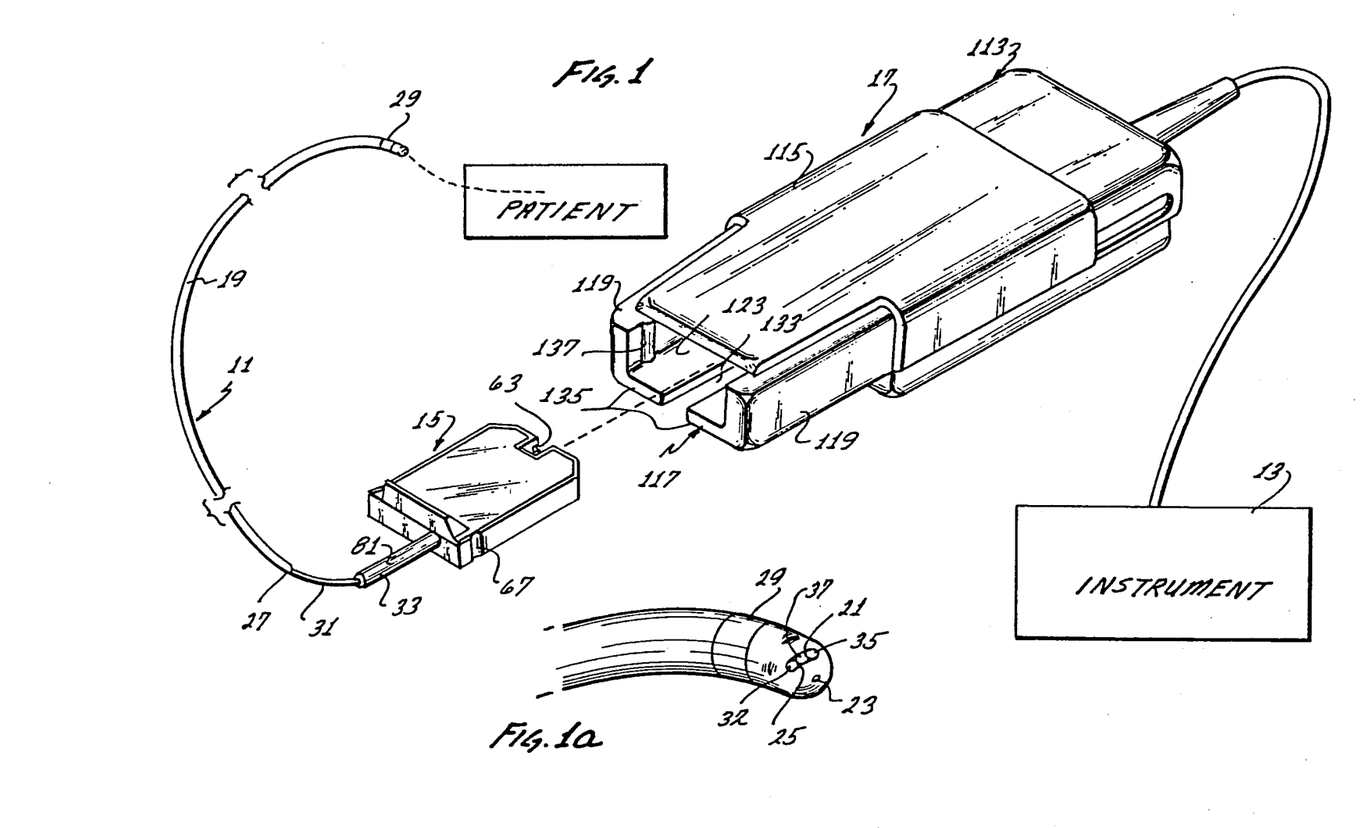
FIG. 1 is a partially schematic, isometric view illustrating an apparatus constructed in accordance with the teachings of this invention.
FIG. 1a is a fragmentary, isometric view of a distal end portion of a catheter.

FIG. 1 shows a catheter 11 which can be releasably coupled to an instrument 13 using a connector body 15 and a receptacle 17. The receptacle 17 may be considered as part of the instrument 13. Although the features of this invention are particularly adapted for use with a catheter, the invention is not limited to use with a catheter, and the particular catheter shown is purely illustrative.

The catheter 11 includes a tube 19 sized to be received within a vein or an artery of a patient and having proximal and distal ends and a plurality of lumens or passages, including passages 21 and 23 extending longitudinally through it. The passage 21 has a distal opening 25 (FIG. 1a) and a proximal opening 27 (FIG. 1). A balloon 29 is provided on the tube 19 adjacent the distal tip of the catheter.

The catheter 11 also includes fiber optic means 31 extending completely through the passage 21 of the tube 19 from the distal opening 25 through the proximal opening 27 to provide a proximal section 33 of the fiber optic means outside of the tube. Of course, other tubing in communication with the other passages of the tube 19 can also exit at the proximal opening 27. Although various constructions are possible, in the embodiment illustrated, the fiber optic means 31 includes fiber optic light conductors 35 and 37 for conducting light to the distal opening 25 and for conducting a light signal away from the distal opening 25, respectively. The distal ends of the light conductors are tightly retained within the passage 21, which is of larger cross section than the two light conductors, by a spacer 32 (FIG. 1a). A catheter of this type can be used to measure the oxygen saturation of blood by determining its color absorption characteristics in accordance with known techniques. To make this determination, the catheter 11 is inserted into the heart of the patient to place the distal opening 25 in the pulmonary artery.

Figure 2:
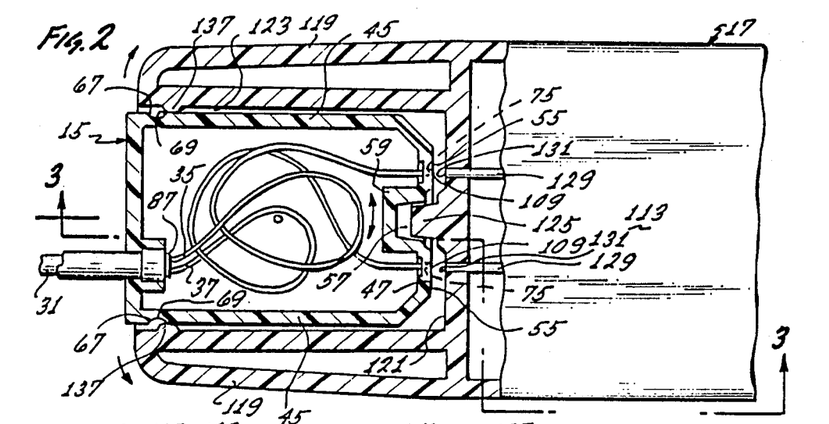
FIGS. 2 and 2a are fragmentary, top plan views of the receptacle and connector body, with the connector body partially and fully inserted into the receptacle, respectively.
Figure 2A:
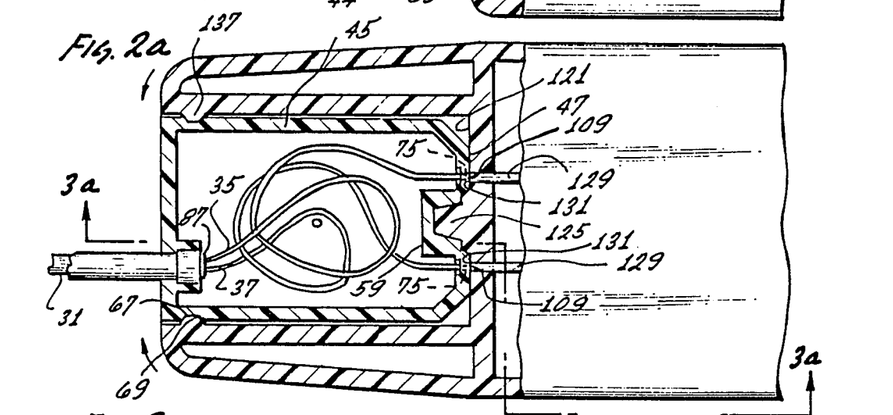
Figure 3:
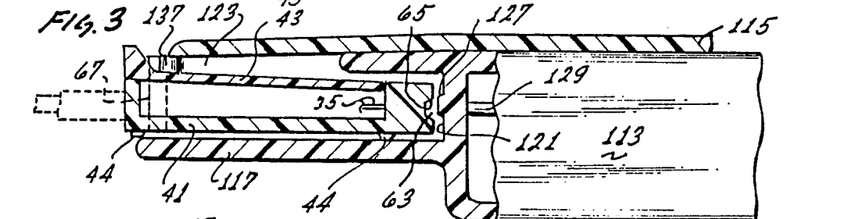
FIGS. 3 and 3a are fragmentary sectional views taken along lines 3—3 and 3a—3a of FIGS. 2 and 2a, respectively.
Figure 3A:
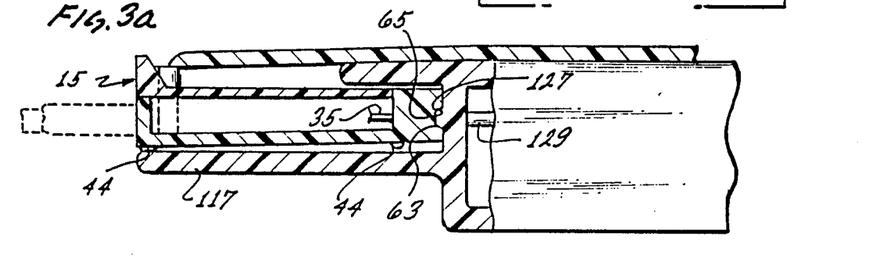
Figures 4, 5:
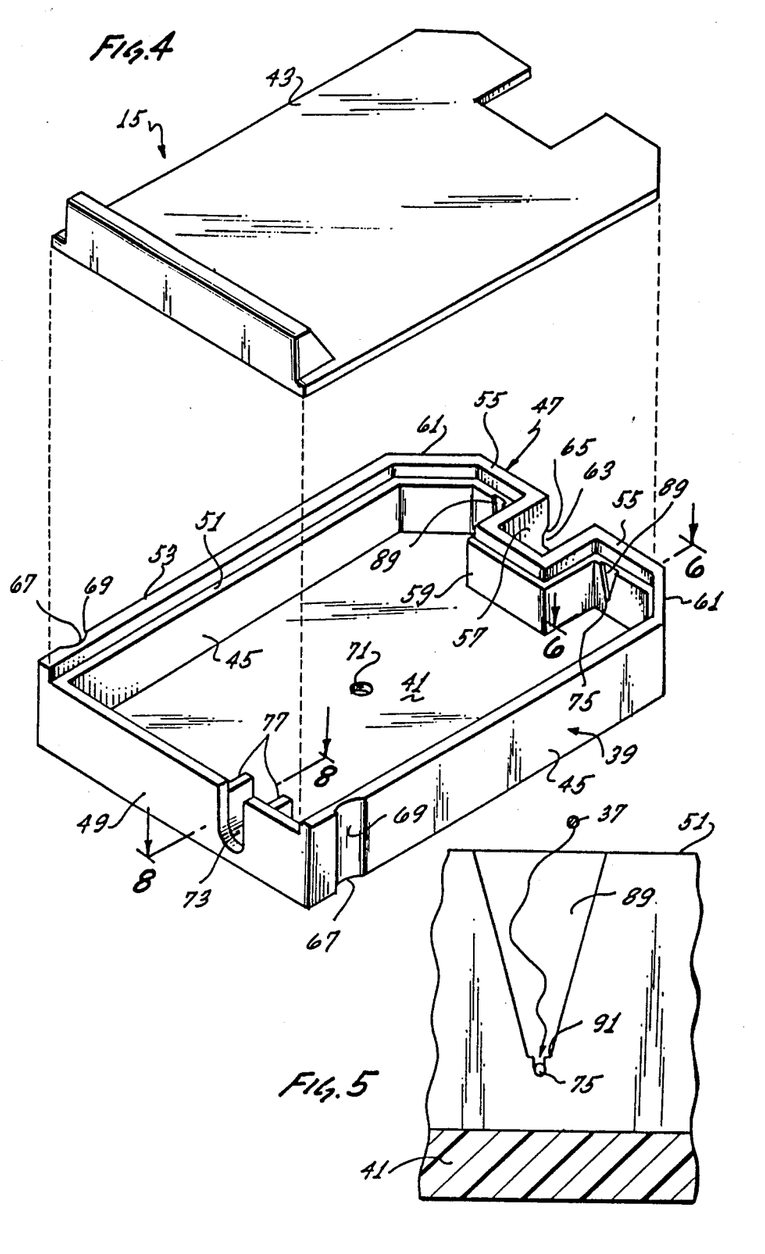
FIG. 4 is an exploded isometric view of the connector body with the light conductors removed.
FIG. 5 is an enlarged, fragmentary sectional view of a portion of the connector body which includes the exit passage.

The proximal section 33 of the fiber optic means 31 is coupled to the connector body 15, and the details of the connector body are shown in FIGS. 2-8a. The connector body 15 has wall means which define an enclosure, and the wall means includes a circumscribing peripheral wall 39, a floor 41 and a cover 43 (FIG. 4). Supporting feet 44 (FIGS. 3 and 3a) extend downwardly from the floor 41. The peripheral wall 39 includes opposed, parallel side walls 45, an end wall or forward face 47 and a trailing end wall 49. The side walls 45 provide outer side surfaces, and the floor 41 and the cover 43 provides bottom and top surfaces, respectively, for the connector body. The peripheral wall 39 extends perpendicular to the floor 41 and has a ledge 51 and a lip 53 projecting from the ledge. The cover 43 is receivable within the lip 53 and onto the ledge 51 with a snap fit to releasably retain the cover in position.

The face 47 includes identical face sections 55 (FIGS. 2 and 4) separated by a tapered gap 57 which narrows as it extends inwardly of the enclosure and which is defined by a channel section 59. The face 47 also has inclined corner sections 61 which join the sections 55 to the side walls 45, respectively.

The face sections 55 have identical recesses 63, respectively, which open into the gap 57 (FIGS. 3, 3a and 4). The face sections 55 are flat and coplanar, except for the recesses 63. Each of the recesses 63 is partially defined by an inclined cam follower surface 65. The other side surfaces of each of the recesses 63 are also inclined and they terminate inwardly in a flat bottom surface.

Each of the side walls 45 has a surface defining a recess or groove 67 in its exterior surface, and each of the grooves has a longitudinal axis which extends perpendicular to the longitudinal axis of the associated side wall. Each of the grooves 67 is identical and is partially defined by a inclined cam surface 69 along the forward or leading side of the groove. The cam surfaces 69 are used as described more fully hereinbelow for connecting the connector body 15 to the rceptacle 17.

The connector body 15 can be of two-piece, molded plastic construction as shown in FIG. 4. The cover 43 is configured to mate with and close the opening at the upper end of the construction formed by the peripheral wall 39 and the floor 41. The floor 41 may have a central aperture 71.

The end wall 49 has an entrance passage 73, and each of the face sections 55 has an identical exit passage 75, with the exit passages being spaced apart in the same direction as the side walls 45. Because the exit passages 75 are identical, only one of them is described in detail herein. As shown in FIG. 8, the end wall 49 has a pair of legs 77 which project inwardly into the enclosure and define shoulders 79 on opposite sides of the entrance passage 73.

The entrance passage 73 cooperates with the proximal section 33 of the fiber optic means 31 as shown in FIG. 8a. Specifically, the proximal section 33 includes a sheet of shrink tubing 81 and a shorter section of shrink tubing 83 shrunk over and glued to the tubing 81. The tubing 83 forms an annular shoulder 85 which engages the shoulders 79 as shown to provide strain relief.

Thus, the proximal section 33 of the fiber optic means 31 passes through the entrance passage 73 and into the interior of the enclosure. As shown in FIGS. 2 and 2a, the light conductors 35 and 37 extend beyond the end of a sheath 87 in which they are encased, and an excess length of both of the light conductors is provided within the enclosure. In this embodiment, each of the light conductors 35 and 37 is in the form of a fine, small diameter optical fiber. The light conductors 35 and 37 extend into the exit passages 75, respectively, and they are retained in these exit pasages with their ends flush with the outer surface 88 (FIG. 6c) of the associated face sections 55.

To facilitate insertion of the light conductors 35 and 37 into the associated exit passage 75, tapered lead-in grooves 89 are provided on the interior surfaces of the face sections 55 as shown in FIGS. 4 and 5. Each of the lead-in grooves 89 is identical and extends from the ledge 51 to the associated exit passage 75, and it progressively narrows as it extends toward such exit passage. In the embodiment illustrated, each of the lead-in grooves 89 tapers linearly, except for a step 91 closely adjacent the exit passage 75. With this construction, the light conductor 37 can be easily inserted into the wide end of the lead-in groove 89 adjacent the ledge 51 and guided toward, and into, the exit passage 75.

Figure 6:
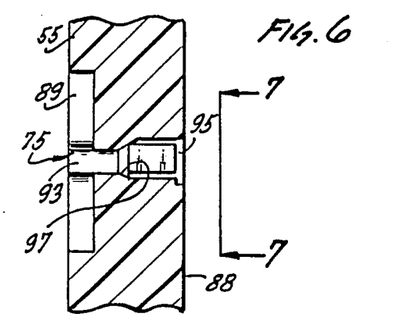
FIG. 6 is an enlarged, fragmentary sectional view taken generally along line 6—6 of FIG. 4.
Figure 7:
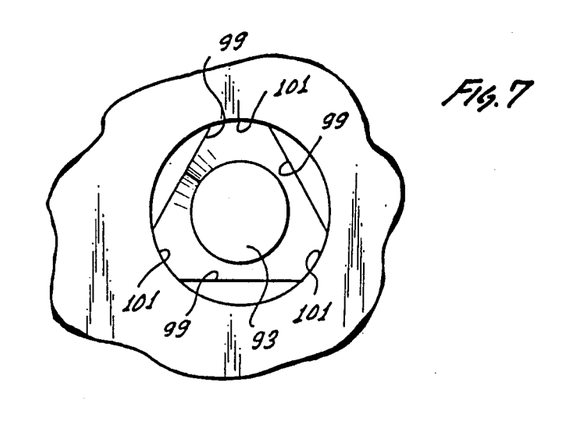
FIG. 7 is an enlarged elevational view taken generally along line 7—7 of FIG. 6.

A prefereed construction of the exit passage 75 is shown in FIGS. 6 and 7. The exit passage 75 has an entrance section 93 of reduced cross section, an exit section 95 of enlarged cross section, a shoulder 97 between these sections, and flat surfaces or surface portions 99 and curved surfaces or surface portions 101 arranged circumferentially in the exit section of the passage. The flat surfaces 99 are set back slightly from the exterior surface 88 of the face section 55 at which the exit passage 75 opens. If desired, a region of the flat surfaces 99 adjacent to the outer surface 88 may be inclined radially inwardly as they extend toward the outer surface 88.

The surfaces 99 and 101 are arranged circumferentially in the exit section 95. Although various constructions are possible, in the embodiment illustrated, there are three identical flat surfaces 99 and they are spaced apart 120 degrees. Each of the curved surfaces 101 is identical and comprises a segment of a cylinder. One of the curved surfaces 101 lies circumferentially between adjacent flat surfaces 99.

The flat surfaces 99 are closer together radially than the surfaces 101. For example, the flat surfaces 99 may be sized and arranged to receive a member of 0.0135 inch diameter, and the curved surfaces 101 may be segments of a cylinder having a diameter of 0.016 inch.

Figure 6A:
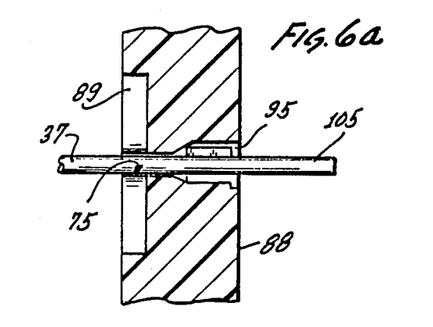
FIGS. 6a-6c are fragmentary, sectional views similar to FIG. 6 illustrating a preferred method of retaining the light conductors in the exit passage.
Figure 6B:
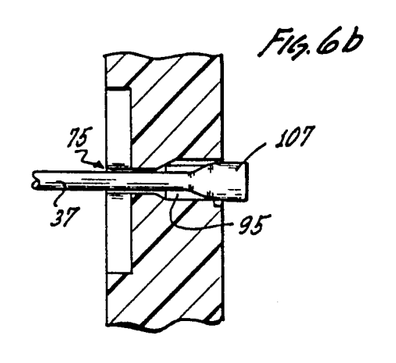

To attach the light conductor 37 to the face section 55, the light conductor 37 is inserted into the exit passage 75 using the lead-in groove 89 and through the exit passage as shown in FIG. 6a. Accordingly, the light conductor 37 has an end portion 105 on the exit section side of the exit passage 75. Next, the end portion 105 is radially enlarged. Although the radial enlarging of the light conductor 37 can be carried out in different ways, this is preferably accomplished by using a light conductor of the type which radially enlarges in response to being heated. For example, an optical fiber comprising an acrylic core and a fluoropolymer sheath will radially expand and axially contract in response to heating. Preferably, the end portion 105 is heated to radially enlarge the end portion to form an enlargement 107 (FIG. 6b) of the desired cross-sectional area which may be frustoconical with the major diameter at the end of the light conductor. for example, a light conductor having a diameter of 0.010 inch can be enlarged to a diameter of about 0.015 inch by exposing the end portion 105 to a temperature of about 550 degrees Fahrenheit and continuing that exposure for about 8 seconds.

Figure 6C:
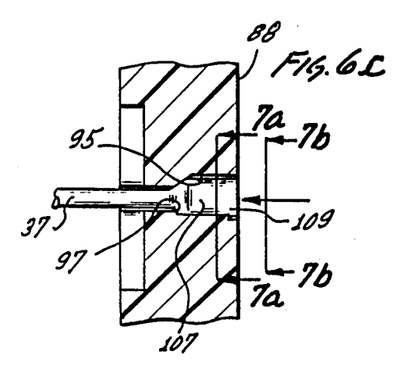
Figure 7A:
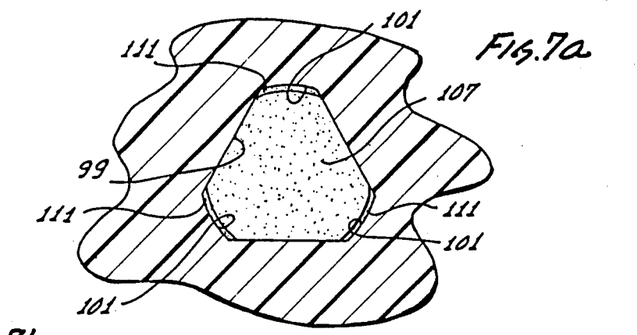
FIGS. 7a and 7b are views taken generally along lines 7a—7a and 7b—7b, respectively, of FIG. 6c.
Figures 7B, 8, 8A:
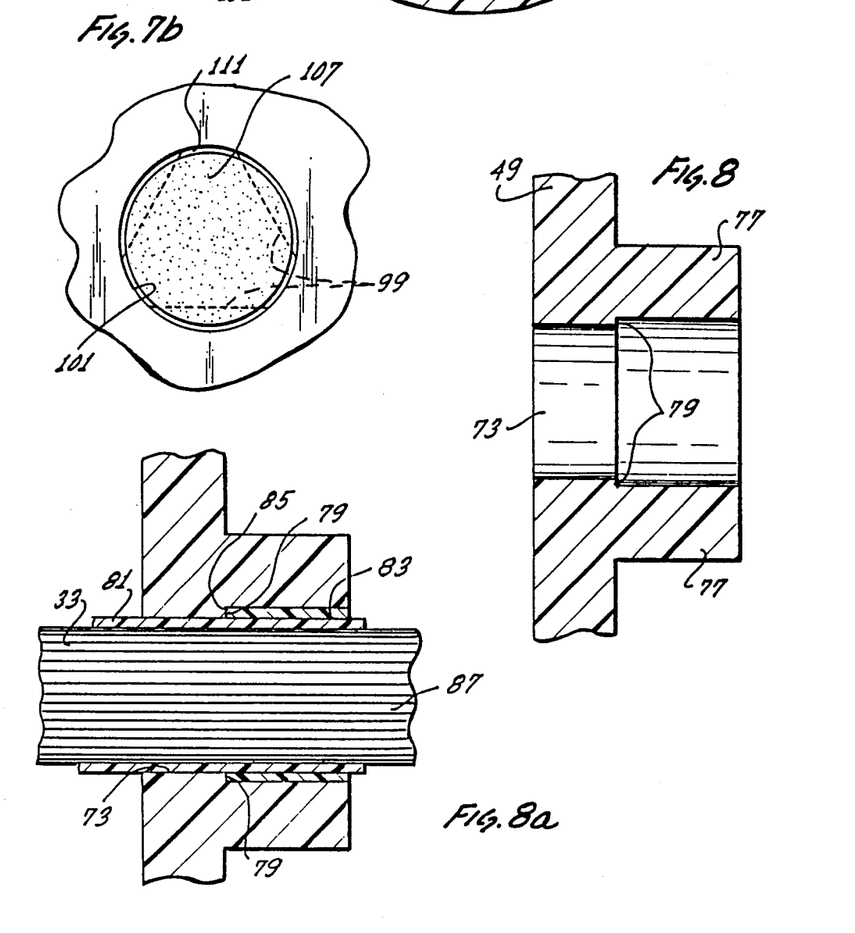
FIGS. 8 and 8a are enlarged fragmentary sectional views taken generally along line 8—8 of FIG. 4 and illustrating the entrance passage empty and with the light conductors installed therein, respectively.

Next, the enlargement 107 is forced into the exit section 95 of the exit passage 75 to compressively engage the enlargement with the flat surfaces 99 as shown in FIGS. 6c, 7a and 7b. Preferably, the enlargement 107 is pushed back into the exit section 95. As shown in FIG. 6c, at the completion of this step, a proximal end 109 of the light conductor 37 is flush with the outer surface 88 and is therefor at a known location on the surface 88.

The enlargement 107 is somewhat deformable and its diameter is greater than the diameter than can be accepted by the flat surfaces 99. Accordingly, the forcing of the enlargement 107 between the flat surfaces 99 displaces material from the enlargement 107 circumferentially to regions 111 (FIG. 7a) between the enlargement 107 and the curved surfaces 101. As shown in FIG. 7a, there are three regions 111, each of which is in the form of a radial gap. Accordingly, the enlargement 107 is frictionally retained in the exit section 95 by the flat surfaces 99 and, in addition, the enlargement 107 at its juncture with the non-enlarged portion of the light conductor 37 defines a shoulder which engages the shoulder 97 to inhibit withdrawal of the light conductor through the entrance section 93. Preferably, a suitable adhesive is applied to the enlargement 107 and/or to the surfaces of the exit passage 75 prior to forcing the enlargement 107 back into the exit section 95. Accordingly, the frictional retention of the enlargement 107 by the flat surfaces 99 serves, in effect, as a fixture to hold the light conductor 37 within the exit passage 75 while the adhesive cures. Inclining regions of the flat surfaces 99 adjacent the outer surface 88 radially inwardly as they extend toward the surface 88 helps to lock the enlargement 107 in the exit passage 75. The flat surfaces 99 also accurately center the light conductors.

The receptacle 17 (FIGS. 1–3a) comprises a body 113 and a cover 115 mounted on the body for slidable movement longitudinally of the body. The body 113, which may be molded from a suitable plastic material, comprises a floor 117, side walls 119 and a face 121 (FIGS. 2–3) cooperating to define a cavity 123 sized to receive the connector body 15. The cavity 123 has an open end opposite the face 121. The face 121 is flat and planar, except for a central wedge-shaped projection 125 adapted to be received within the gap 57 and for cam surfaces 127 adapted to cooperate with the cam follower surfaces 65, respectively. Light conductors 129 extend within the receptacle 17 and have their ends mounted in and flush with the face 121 at locations 131, respectively. The locations 131 are arranged to be in confronting and substantially aligned relationship with the exit passages 75, respectively, when the connector body 15 is received within the cavity 123.

The floor 117 has a slot 133 to separate the adjacent portions of the receptacle 17 into resilient sections 135 (FIG. 1). A projection 137 is mounted on and carried by each of the side walls 119. The resilient sections 135 and the projections 137 form biasing means or a biasing member capable of exerting inward force on the connector body 15. Of course, the biasing means can be formed in other ways.

To attach the connector body 15 to the receptacle 17, the connector body is advanced into the cavity 123 and slid in a generally forwardly direction to bring the faces 47 and 121 closer together. During this sliding movement, the feet 44 of the connector body 15 slide along the floor 117 of the receptacle 17, and the inner surfaces of the side wlls 119, the floor 117, the projection 125 and the confronting surfaces of the connector body 15 form guide means for guiding the connector body along a path in the cavity 123 to place the faces 47 and 121 in confronting relationship and to bring the proximal ends 109 of the light conductors 35 and 37 into engagement with the locations 131. As the connector body 15 is advanced into the cavity 123, the side walls 45 of the connector body 15 engage the projections 137 and urge the resilient sections 135 resiliently away from each other. When the proximal ends 109 are nearly in engagement with the locations 131 as shown in FIGS. 2 and 3, the projections 137 engage the cam surfaces 69 and urge the connector body 15 farther into the cavity 123 to place the faces 47 and 121 into engagement and to place the proximal ends 109 into engagement and substantial axial alignment with the locations 131. The projections 137 cooperate with the groove 67 to retain the connector body 15 in the cavity 123 of the recepacle 17.

In the position shown in FIGS. 2 and 3, the cam follower surfaces 65 are nearly in engagement with the cam surfaces 127. The final advancing motion of the connector body 15 into the cavity 123 causes the cam follower surfaces 65 to engage the cam surfaces 127 to lift the forward end of the connector body 15, and in particular the forward foot 44, off of the floor 117 as shown in FIG. 3a. This elevation of the forward end of the connector body 15 accurately positions the exit passages 75 and brings them into correct alignment with the locations 131. The cam surfaces 127 and the cam follower surfaces 65 also cooperate to assist in holding the connector body 15 in the desired orientation within the cavity 123.

The cam surfaces 127 and the cam follower surfaces 65 form a portion of the guiding means for guiding the connector body 15 into the proper location within the cavity 123. Thus, the path along which the connector body 15 moves extends in a first direction, which is generally along the longitudinal axis of the body 113, until the cam follower surfaces 65 contact the cam surfaces 127 and then in a second direction along the cam surfaces 127. This latter portion of movement of the connector body 15 occurs when the faces 47 and 121 are closely adjacent and may be under the influence of the biasing action of the receptacle 17 and the cooperation between the projections 137 and the cam surfaces 69.

The cooperation between the projections 137 and the cam surfaces 69 automatically draws the connector body 15 completely into the correct seated position within the cavity 123. This final movement is accompanied by an audible "click" to inform the operator of the correct seating. The force provided assures that the optical portions, i.e., the proximal ends 109 and the locations 131, will be in contact and in proper registry.

In use, the instrument 13 may provide light through one of the light conductors 129 to the light conductor 35, and this light is transmitted through the interface at the faces 47 and 121 to the light conductor 35 which transmits it to the distal opening 25. Assuming that the catheter 11 is correctly positioned within a vein or artery within the patient, the light at the distal opening from the light conductor 35 is directed against the patient's blood. The blood reflects light into the light conductor 37, and the reflected light forms a signal having a characteristic related to the absorption characteristics of the blood. The light signal is transmitted throught the light conductor 37 and into the other of the light conductors 129. The light signal is converted to an electrical signal within the receptacle 17 and transmitted to the instrument 13 for processing in accordance with known techniques to determine the oxygenation of the blood.

FIGS. 9-14 show a second embodiment of the invention which is identical to the embodiment of FIGS. 1-8a in all respects not shown or described herein. Portions of the second embodiment corresponding to portions of the first embodiment are designated by corresponding reference numerals followed by the letter "a."

Structurally, the primary differences between the two embodiments are in the construction of the recesses 67a and the projections 137a and in the addition of self-test grooves 201. Functionally, the second embodiment differes primarily from the first embodiment in the manner in which the connector body 15a is moved into and retained within the cavity 123a of the receptacle 17a and in the provision of a testing position.

Figures 9, 9A, 10, 12, 14:
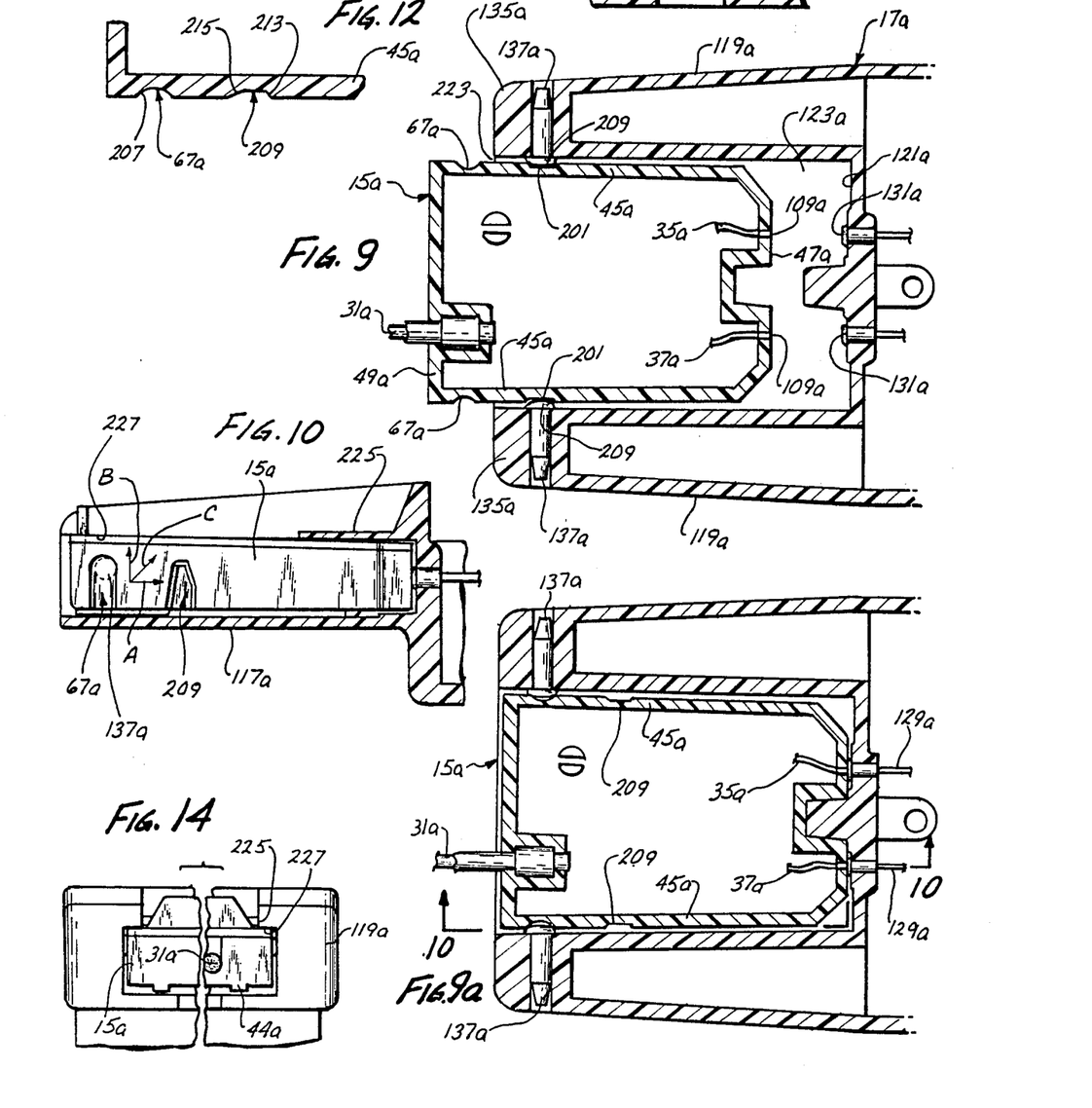
Figure 11:
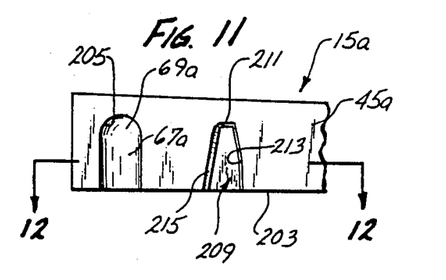
FIG. 11 is a fragmentary, side elevational view of the connector body.
Figure 13:
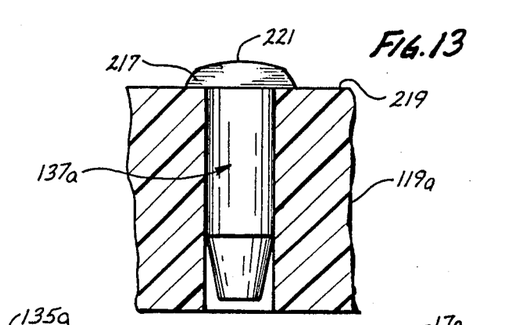
FIG. 13 is an enlarged, fragmentary sectional view showing a portion of the receptacle and the projection.

The recesses 67a are formed in the side walls 45a, respectively, closely adjacent the trailing end wall 49a. The recesses 67a are identical, and so only one of them is described in detail herein. The recess 67a extends from a lower edge 103 (FIG. 11) of the side wall 45a part way across the side wall to a closed, part-spherical end 205. The lower end of the recess 67a opens at the lower edge 203. The part-spherical, closed end 205 forms an inclined surface which closes the upper end of the recess 67a and at least the portion of the inclined surface at the upper, forward corner of the recess 67a as viewed in FIG. 11 forms the cam surface 69a. The regions of the recess 67a below the part-spherical surface are formed by a part-cylindrical surface 207 (FIG. 12).

The connector body 15a also has identical self-test recesses or grooves 209 in the side walls 45a, respectively, which are spaced forwardly from the recesses 67a in the associated side wall. Although various cnstructions of the test recess 209 are possible, preferably, each of the test recesses opens at the lower edge 203 in order to facilitate molding and has a closed upper end 211. The test recess 209 has a sloping forward wall 213 and a sloping trailing wall 215, with the angle of incline of the sloping wall 215 being less than the angle of incline of the sloping wall 213 to facilitate further forward advancing movement of the connector body 15a in the cavity 123a.

The receptacle 17a has projections 137a in the form of pins mounted on, and carried by, each of the side walls 119a. The projections 137a are identical, and as shown most clearly in FIG. 13, each of them has a head 217 which projects from a inner side surface 219 and a curved, but relatively flat, surface 221. The pin, or at least the head 217 thereof, is preferably constructed of metal or other harder material than the side walls 45a of the connector body 15a.

The cavity 123a of the receptacle 17a has an open end 223, and the face 121a is spaced in a forwardly direction from the open end 223. The receptacle 17a has a partial roof 225 (FIG. 10) over an inner portion of the cavity 123a and ledges 227 (FIG. 14) along the opposite side edges of the upper end of the cavity 123a. To facilitate cleaning, the cover 115 of the receptacle 17 of FIGS. 1-8a is eliminated from the receptacle 17a. As explained more fully hereinbelow, the ledges 227 and the face 121a form stops, which lie in transverse planes and against which the connector body 15a is resiliently urged when the connector body is in the position of FIG. 9a.

In use, the connector body 15 can be manually inserted into the opening 223 and slid in a forwardly direction toward the face 121a of the receptacle 15a as described in connection with FIGS. 1-8a. During this time, the heads 217 of the projections 137a resiliently bear against the outside surfaces of the side walls 45a, respectively, as a result of an inward biasing force applied by resilient sections 135a, to resist such forward movement of the connector body. When the connector body 15a is advanced to the position of FIG. 9, the heads 217 of the projections 137a are at least partially received in the test grooves 209, respetively, as shown in FIG. 9 to releasably retain the connector body in the test position of FIG. 9. Reaching of the test position is audibly made manifest by a click as the heads 217 enter the associated test grooves 209. In this position, the locations 131a and the proximal ends 109a are spaced so that light can be transmitted from the locations 131a to the connector body 15a and reflected back to the locations 131a from the connector body so that the optics and electronics of the associated instrument 13 (FIG. 1) can be checked before the catheter 11 is inserted into the patient. Of course, other functions can be carried out using the test recess or another recess.

The connector body 15a can be advanced to the monitor position of FIG. 9a by pushing the connector body 15a forwardly. The cam surfaces 69a cooperate with the heads 217 of the projections 137a, respectively, for urging the connector body farther into the cavity 123a along a predetermined path "c" (FIG. 10). This path has components which extend toward the forward face 121a of the receptacle and the forward face 47a of the connector body 15a as indicated by the arrow "A" in FIG. 10 and upwardly as indicated by the arrow "B" in FIG. 10. The resultant of the components "A" and "B" acts at some intermediate angle along the path or direction "C" shown in FIG. 10. Consequently, the connector body 15a is urged upwardly against the ledges 227 and forwardly against the forward face 121a of the receptacle 17a. Of course, in the monitor position of FIG. 9a, the proximal ends 109a and the associated locations 131a are in an aligned predetermined, optically coupled relationship to each other as described above in connection with FIGS. 1–8a.

More specifically, the heads 217 of the projections 137a engage the part-spherical cam surfaces 69a, respectively, at the upper, forward end (FIGS. 10 and 11) of the recesses 67a. Consequently, because of the inclined nature of the cam surfaces 69a, the trailing end of the connector body 15a is urged along the path "C.". The forward end of the connector body 15a also tends to be retained by the cooperation between the cam follower surfaces 65 of the connector body and the cam surfaces 127 of the receptacle in the same manner as described above in connection with Figs. 1–8a. The cam follower surfaces 65 and the cam surfaces 127 are not visible in FIGS. 9–14 which illustrate the second embodiment of the invention.

Viewed from a different perspective, the side walls 45a and the proximal ends 109a are spaced apart in a first direction, and the biasing force of the side walls 119a of the receptacle 17a acts inwardly in the first direction. The first direction is transverse, or generally perpendicular, to the forward direction. The component of motion "B" (FIG. 10) is generally transverse or perpendicular to both the first direction and the forward direction.

Although exemplary embodiments of the invention have been shown and described, many changes, modifications and substitutions may be made by one having ordinary skill in the art without necessarily departing from the spirit and scope of this invention.

I claim:

1. An apparatus comprising:
    at least one elongated light conductor;
    a connector body having an exterior face;
    means for mounting the light conductor on the connector body with an end of the light conductor being adjacent the face and capable of transmitting light to or from a location on said face;
    a receptacle having a cavity with an open end for receiving the connector body, a face spaced in a generally forwardly direction from said open end and partly defining said cavity and means for transmitting light to or from a location on said face of said receptacle;
    said connector body being receivable in the cavity with said faces in confronting relationship and said locations in a predetermined relationship to each other so that light can be transmitted from one of said locations to the other of said locations;
    one of said connector body and said receptacle having a surface defining a recess, at least a part of said surface being a cam surface;
    a projection carried by the other of said connector body and said receptacle and adapted to be at least partly received in said recess;
    said receptacle having resilient means for urging the projection in a second direction extending into the recess, said second direction being generally transverse to said forwardly direction; and
    said cam surface cooperating with said projection for urging said connector body in a direction which has components which extend farther into said cavity and in a third direction which is generally transverse to both the forwardly direction and the second direction whereby the connector body is retained in said cavity with said locations in said predetermined relationship and said cavity allowing the connector body to move in said third direction in response to the cooperation between the cam surface and the projection.

2. An apparatus as defined in claim 1 wherein the recess is on the connector body and the projection is on the receptacle.

3. An apparatus as defined in claim 2 wherein the projection includes a pin having a somewhat flattened head which is adapted to be received in the recess.

4. An apparatus as defined in claim 2 wherein the connector body has a peripheral wall which includes said exterior face thereof and first and second side walls, said recess being in said first side wall and said second side wall having a second recess therein, said apparatus includes a second projection receivable in the second recess for urging the connector body farther into the cavity and in said third direction, one of said projections confronting one of said side walls and being engaged thereby when the connector body is being moved in generally said forwardly direction and at least the part of said one projection which engages said one side wall is harder than said one side wall.

5. An apparatus as defined in claim 4 wherein said cam surface includes an inclined surface at a corner of the associated recess and said recess extends only part way across the associated side wall.

6. An apparatus as defined in claim 1 wherein said cam surface includes an inclined surface at a corner of said recess, said inclined surface being engageable with said projection to urge said connector body in a direction which has components which extend farther into said cavity and in said third direction.

7. An apparatus as defined in claim 6 wherein the connector body has a peripheral wall, said recess extends part way across the peripheral wall, one end of the recess opens adjacent an edge of the peripheral wall and the other end of the recess is at least partly closed, and the inclined surface is at said other end of the recess.

8. An apparatus as defined in claim 1 including a second recess in the connector body spaced from the first-mentioned recess and cooperable with the projection to releasably retain said locations in a second predetermined relationship whereby the connector body and receptacle can cooperate to perform another function.

9. An apparatus as defined in claim 1 wherein the receptacle includes a stop and the connector body is urged in said third direction against said stop by the cooperation between the recess and the projection.

10. An apparatus as defined in claim 1 including a second elongated light conductor mounted on said connector body with an end of the second light conductor being adjacent the face of the connector body and capable of transmitting light to or from a location on said face of the connector body, said ends of said light conductors being spaced apart generally in said second direction, said end of the second light conductor being optically coupled to a location on the receptacle when the connector body is received in the receptacle.

11. An apparatus comprising:

at least one fiber optic light conductor;

a connector body having an exterior face;

means for mounting the fiber optic light conductor on the connector body with an end of the fiber optic light conductor being adjacent the face and capable of transmitting light to or from a location on said face;

a receptacle having a cavity with an open end for receiving the connector body, a face spaced in a generally forwardly direction from said open end and partly defining said cavity and means for transmitting light to or from a location on said face of said receptacle;

guide means at least partially on the receptacle for guiding the connector body along a path in the cavity to place said faces in confronting relationship and said locations substantially into engagement;

said connector body having a cam surface at least partially defining a recess; and said receptacle having biasing means including a projection cooperable with said cam surface when the connector body is in the cavity of the receptacle and said locations are nearly in engagement for urging the projection in a second direction into the recess, said projection and cam surface cooperating to urge the connector body in a direction which has components which extend farther into the cavity and in a third direction generally transverse to both the forwardly direction and the second direction whereby said locations on said faces are placed in substantial engagement and said cavity allowing the connector body to move in said third direction in response to the cooperation between the cam surface and the projection.

12. An apparatus as defined in claim 11 wherein the projection includes a pin having a somewhat flattened head which is adapted to be received in the recess.

13. An apparatus as defined in claim 11 wherein said cam surface includes an inclined surface at a corner of said recess, said inclined surface being engageable with said projection to urge said connector body in a direction which has components which extend farther into said cavity and in a third direction.

14. An apparatus as defined in claim 13 wherein the connector body has a peripheral wall, said recess extends part way across the peripheral wall, one end of the recess opens adjacent an edge of the peripheral wall and the other end of the recess is at least partly closed, and the inclined surface is at said other end of the recess.

15. An apparatus connectible to an instrument wherein the instrument has a receptacle with a cavity, a face partly defining the cavity, means for transmitting light to or from locations on the face of the receptacle, and a resilient biasing member, said apparatus comprising:

fiber optic means for conducting light along its length and including first and second fiber optic light conductors with each of the light conductors having a proximal end;

a connector body having top and bottom surfaces spaced apart in a first direction and a peripheral surface which includes a forward face and generally opposite side surfaces spaced apart in a second direction and said connector body including means for retaining the proximal ends of the light conductors adjacent first and second locations, respectively, of the forward face, said proximal ends of the fiber optic light conductors being spaced apart generally in said second direction whereby said proximal ends can be optically coupled to said locations on said face of the receptacle; and a cam surface on at least one of said side surfaces at least partly defining a recess for cooperation with the resilient biasing member when the connector body is in the cavity for urging the connector body along a path having components which extend toward the forward face and in said first direction to place said proximal ends in optically coupled relationship with said locations of the receptacle and said connector body having dimensions in said first direction which are small enough in relation to the cavity so that the connector body can move in said first direction in response to said cooperation between the cam surface and the resilient biasing member.

16. An apparatus as defined in claim 15 wherein said cam surface includes an inclined surface at a corner of said recess, said inclined surface being engageable with the resilient biasing member for urging the connector body farther along said path.

17. An apparatus as defined in claim 15 wherein said recess extends part way across the peripheral wall, one end of the recess opens adjacent an edge of the peripheral wall and the other end of the recess is at least partially closed and the resilient biasing member cooperates with said other end of the recess.

18. An apparatus as defined in claim 15 including a test recess in said one side surface spaced from the cam surface and cooperable with the biasing member to releasably retain the connector body and the receptacle in a predetermined relationship.

19. An apparatus as defined in claim 15 including a second cam surface on the other of said side surfaces partially defining a recess.

20. An apparatus connectible to an instrument, said apparatus comprising:

fiber optic means for conducting light along its length;

a connector body for use in coupling the fiber optic means to the instrument;

said connector body including wall means defining an enclosure and an entrance passage and an exit passage in the wall means, the fiber optic means extending through the entrance passage into the enclosure and into the exit passage, said fiber optic means having a proximal end within or closely adjacent the exit passage whereby said proximal end of the fiber optic means can be optically coupled to a selected part of the instrument;

means for retaining the fiber optic means in said exit passage;

said wall means including a peripheral wall, said peripheral wall including a face and first and second generally opposed side walls and said exit passage opening at said face;

each of said side walls having a surface defining a recess for use in connecting the connector body to the instrument; and at least one of the recesses extending part way across the peripheral wall, one end of said one recess opening adjacent an edge of the peripheral wall and said surface includes an inclined surface adjacent the other end of said one recess, said other end of said one recess being at least partly closed by said inclined surface.

21. An apparatus as defined in claim 20 wherein said fiber optic means includes first and second fiber optic light conductors, said exit passage is a first exit passage, said enclosure has a second exit passage opening at said face and said second fiber optic light conductor is received in the second exit passage and retained therein, and said exit passages are spaced apart in the same general direction as the side walls.

22. An apparatus as defined in claim 20 including a test recess in one of said side walls, said test recess being spaced forwardly from the other recess in the associated side wall.

23. An apparatus as defined in claim 20 including an elongated tube sized to be received within a vein or artery and having proximal and distal ends and at least one elongated passage with proximal and distal openings, said fiber optic means being partially in said passage and being capable of conducting light to said distal opening and from said distal opening, said fiber optic means extending through said proximal opening to provide a proximal section of said fiber optic means outside of said tube, at least a portion of the proximal section extending through said entrance passage and into said enclosure.

24. An apparatus comprising:
at least one elongated light conductor;
a connector body having an exterior face generally opposite side surfaces and top and bottom surfaces;
means for mounting the light conductor on the connector body with an end of the light conductor being adjacent the face and capable of transmitting light to or from a location on said face;
a receptacle having a cavity with an open end for receiving the connector body, a face spaced in a generally forwardly direction from said open end and a stop generally transverse to said face, said face and said stop partly defining said cavity and means for transmitting light to or from a location on said face of said receptacle;
said connector body being receivable in the cavity with said faces in confronting relationship and said locations in a predetermined relationship to each other so that light can be transmitted from one of said locations to the other of said locations, one of said top and bottom surfaces confronting said stop when the connector body is received in said cavity;
one of said side surfaces of said connector body and said receptacle having a surface defining a recess, at least a part of said surface being a cam surface;
a projection carried by the other of said side surfaces of said connector body and said receptacle and adapted to be at least partly received in said recess;
said receptacle having resilient means for urging the projection in a second direction into the recess said second direction being generally transverse to said biasing direction; and
said cam surface cooperating with said projection for urging said faces together and urging said one of said top and bottom surfaces against said stop whereby the connector body is retained in said cavity with said locations in said predetermined relationship.

* * * * *